United States Patent [19]

Jacobson et al.

[11] 4,260,687

[45] Apr. 7, 1981

[54] DIAGNOSTIC DEVICE

[75] Inventors: Donald P. Kronish, Rockaway; Walter E. Jacobson, Morris Plains; Doris B. Taylor, Parsippany; William D. Young, Montclair, all of N.J.

[73] Assignee: Warner-Lambert Company, Morris Plains, N.J.

[21] Appl. No.: 721,021

[22] Filed: Sep. 7, 1976

[51] Int. Cl.³ ............................................. C12M 1/20
[52] U.S. Cl. ....................................... 435/301; 422/61; 435/32; 435/34; 435/299; 435/300; 435/810
[58] Field of Search ................ 195/127, 139, 103.5 M, 195/103.5 R; 23/259 R; 435/29, 30, 32, 33, 34, 299, 300, 301, 810; 422/61

[56] References Cited

U.S. PATENT DOCUMENTS

| 3,713,779 | 1/1973 | Sirago et al. ...................... 23/259 |
| 3,752,743 | 8/1973 | Henshilwood ............... 195/103.5 M |
| 3,799,742 | 3/1974 | Coleman ........................... 23/253 R |
| 3,895,661 | 7/1975 | Praglin et al. ...................... 23/259 X |
| 3,925,166 | 12/1975 | Blume ................................. 195/139 |
| 3,961,899 | 6/1976 | Trinedi et al. .................... 195/127 X |
| 3,983,006 | 9/1976 | Acker et al. ...................... 195/127 X |
| 4,018,652 | 4/1977 | Lanham et al. ............... 195/103.5 M |

FOREIGN PATENT DOCUMENTS 1220083   6/1966   Fed. Rep. of Germany ........... 195/127

Primary Examiner—Robert J. Warden
Attorney, Agent, or Firm—Jeremiah J. Duggan; Stephen A. Schneeberger

[57] ABSTRACT

A diagnostic device for measuring biochemical characteristics of microorganisms. A first chamber is provided into which is inoculated a test suspension containing an unknown organism. First passage means selectively provides liquid communication between the first chamber and a second chamber. The second chamber provides for contacting the liquid suspension with a substrate reagent which is located therein. Second passage means connects the second chamber to a third and selectively allows liquid communication therebetween. The third chamber may contain a suitable detection means for identifying the biochemical characteristics of the reacted test suspension when brought into contact therewith.

23 Claims, 5 Drawing Figures

DIAGNOSTIC DEVICE

BACKGROUND OF THE INVENTION

The present invention relates to the collection and identification of microorganisms and, while it is most suitably described in such context, it must be realized that its structure may be applied in other uses without departing from its inventive concept.

Bacterial diseases are diagnosed and treated by the isolation and identification of causative microorganisms. Conventionally, medical therapy should only be initiated after determination of the etiologic agent. This determination is based primarily on clinical information, but confirmatory laboratory data should always be sought to aid and permit appropriate management of the infective disease. Clinical tests for bacterial identification depend upon comparison of a number of physiological, morphological, and positive and/or negative biochemical reactions for the suspect etiologic agent and comparing these with the reactions of known species. To accomplish this task, it is necessary to obtain specimen cultures of the organism from such sources as sputum, blood, urine, etc., and submit of these samples to identifying procedures.

This means of identification is complex and time-consuming and concomitantly prone to possible error and mis-identification. Moreover, the time-consuming nature of the many tests which must be conducted places a burden on the cost of laboratory operation and excessive employment of skilled personnel for long periods of time.

Various methods and apparatus have been employed in an attempt to facilitate the identification of micoorganisms. These are primarily directed to expediting the cumbersome process and rendering the identification more positive. One such device is described in U.S. Pat. No. 3,784,448, which discloses a separately compartmented tube containing pre-prepared culture media for differential identication of microorganisms, particulary of the Enterobacteriaceae family. In using this device, a rigid rod-like member containing a culture of the organism is withdrawn through the tube thereby inoculating each of the chambers. This prior art device is limited by the number of tests available for use in the unit and by its cost as well as storage and stability problems.

To date, a most successful advance in this area of clinical laboratory testing involves the use of bibulous paper or other absorbent substrate impregnated with reagents which detect the presence of specific enzymes or metabolic end products characteristic of certain microorganisms. These reagents include a substrate to be acted on by a specific bacterial enzyme and a detection system which reacts with the metabolic end product to yield a readily identifiable color change. U.S. Pat. Nos. 3,122,480, 3,341,427, 3,359,180, 3,378,346, 3,597,321, 3,616,258, 3,645,853 and 3,649,461, which are incorporated in this application by reference, and modifications thereof disclose the preparation and formulation of the various substrate and detection reagents as well as their application to the identification of certain organisms.

A typical application of these techniques involves the following materials and process steps:

1. Paper strips containing suitable substrate and detection reagents are prepared for a number of specific biochemical tests, for example, Voges-Proskauer, nitrate reduction, phenylalanine deaminase, urease, indole, lysine decarboxylase, etc.

2. Test tubes corresponding to the number and order of the tests to be performed are placed in a rack.

3. Bacterial colonies cultured on or in a suitable nutrient, for example, an agar medium, are transferred to and suspended in a tube containing 0.3 ml. of saline for each test to be used. The resultant suspension should have a turbidity approximately equal to a Kirby Baver Standard.

4. Approximately 0.3 ml. of the suspension is pipetted into each of the test tubes.

5. Test strips corresponding to the specific test are added to each of the test tubes and incubated therein for approximately four hours at a temperatures of 35°–37° C.

6. The positive or negative indication of the test is then read from the color of the substrate zone where appropriate, as for example in the lysine decarboxylase test, or the tube is tipped so that the incubated suspension moistens the detection zone where again the color change or absence thereof gives rise to a positive or negative indication, as in the Indole Test, for example.

This test procedure has proven extremely successful, giving accuracy results as good as standard laboratory procedures in a much shorter time. To aid in the determination of the exact organism involved based upon the probabilities determined by each of the specific tests, U.S. Pat. No. 3,957,586 describes one type of an identification system providing for rapid and accurate determination of the causative agent. This system employs a number of punch-coded test data cards which, when placed in registration, give an indication as to the identification of the organism involved according to known principles of Boolean logic. Another approach is the use of a computer program dictionary, based on actual number systems, to provide probability of identification.

It is to further enhance and facilitate the foregoing test procedure that the present invention is directed. Although the rapid reagent-impregnated strip test identification procedure has greatly shortened the time involved and increased the accuracy of organism identification, it is considered that this test may be further enhanced by the utilization of a device which would obviate the need for a plurality number of test tubes as well as the commensurate time and care needed in their handling, cleaning and preparation. The invention envisions a device designed for ease of handling while still allowing rapid and accurate identification.

It is therefore an object of the present invention to provide an improved diagnostic device for the rapid and accurate identification of microorganisms. It is another object of the invention to provide a unitary disposable device for the performance of a series of biochemical tests. It is yet another object of the present invention to provide a device which facilitates rapid and easy inoculation with a test specimen and visual assessment of the test results. Yet another object of the present invention is to provide a test device containing therein substrate and/or detection reagents for the identification of microorganisms.

SUMMARY OF THE INVENTION

In overcoming the problems associated with prior art devices and in achieving the stated objects, the present invention contemplates a diagnostic device which utilizes a first chamber for containing a test suspension.

The first chamber is connected through first passage means to a second chamber for contacting the test suspension with a suitable substrate reagent during the incubation period. The first passage means selectively provides liquid communication between the first and second chambers. A third chamber for contacting the reacted test suspension with a suitable detector is connected to the second chamber by a second passage means which similarly selectively provides for liquid communication therebetween.

The invention further contemplates a disposable frame or support structure in which are mounted or integrally formed the chambers and interconnecting passage means. This structure provides a first chamber in the form of an open-top well into which is inoculated a test suspension of a bacterial culture. The second chamber, which is again an open-top well, is connected to the first well by a first passage means comprising a channel. In the base of the channel a ramp structure is formed, the inclination of which is to prevent passage of liquid from the first well to the second well when the test structure is in a normal plane. Within the second well a substrate reagent may be placed which reacts with the culture during an inoculation step to produce typical metabolic end products for the test under consideration. After incubation of the culture in the second well, the suspension is communicated through a second passage means or channel to a third chamber or open-top well wherein the suspension produces a specified color reaction in a detection reagent. The position of the third well with respect to the second is selected so as to provide liquid communication in the second channel only when the device assumes a specific spatial orientation. The third well may be connected to a fourth chamber for taking up excess test suspension, and a venting means is provided for the escape of air as the inoculum is transferred from the first well to the second well.

In a particular embodiment, the bases of the well and the interconnecting channels are found in parallel planes and the axes of the wells are substantially orthogonal to the plane of the supporting structure. Both the wells and the channels are open for visual inspection, the apertures being co-planar with the top surface of the supporting structure. A clear visually transparent member is used to seal the first channel and the second, third and fourth chambers as well as their interconnecting channels and prevent loss of contents. The first well or chamber is maintained in an open condition in order to permit inoculation with the test suspension. A hinged cover member is mounted along one margin of the support structure and results in closure of the open inoculation chamber when brought into complementary contact with the top surface of the supporting structure. The inner surface of the cover member may be provided with a bibulous or absorbent material to prevent leakage of the test suspension when in a closed position. A plurality of diagnostic devices may be incorporated on a single support structure to enable the accomplishment of a plurality of specific biochemical tests.

Another aspect of the present invention is directed to a method for determining the identification of specific microorganisms. In this method, a test suspension formed from a bacterial culture derived from certain body fluids or specimens is inoculated into a first chamber. The test chamber is caused to assume a particular spatial orientation resulting in the passage of the liquid suspension through a channel or first passage means to a second chamber in which it is reacted with a selected substrate designed to provide a known reaction to the organism involved. After the suspension is incubated with the reagent for a predetermined period, the second chamber is repositioned to another spatial orientation causing the liquid in such chamber to communicate with a third chamber containing a detection reagent. The color reaction of the detection reagent indicates a positive or negative test and thereby provides information as to the identity of the organism.

The objects and features of the present invention will be apparent upon study of the detailed specification hereafter set forth when taken in conjunction with the drawings. The drawings are intended to be exemplary of the invention and utilize standard drawing symbols and consistent numbering throughout the different views for ease of understanding.

DESCRIPTION OF THE PREFERRED EMBODIMENT

Figure 1:
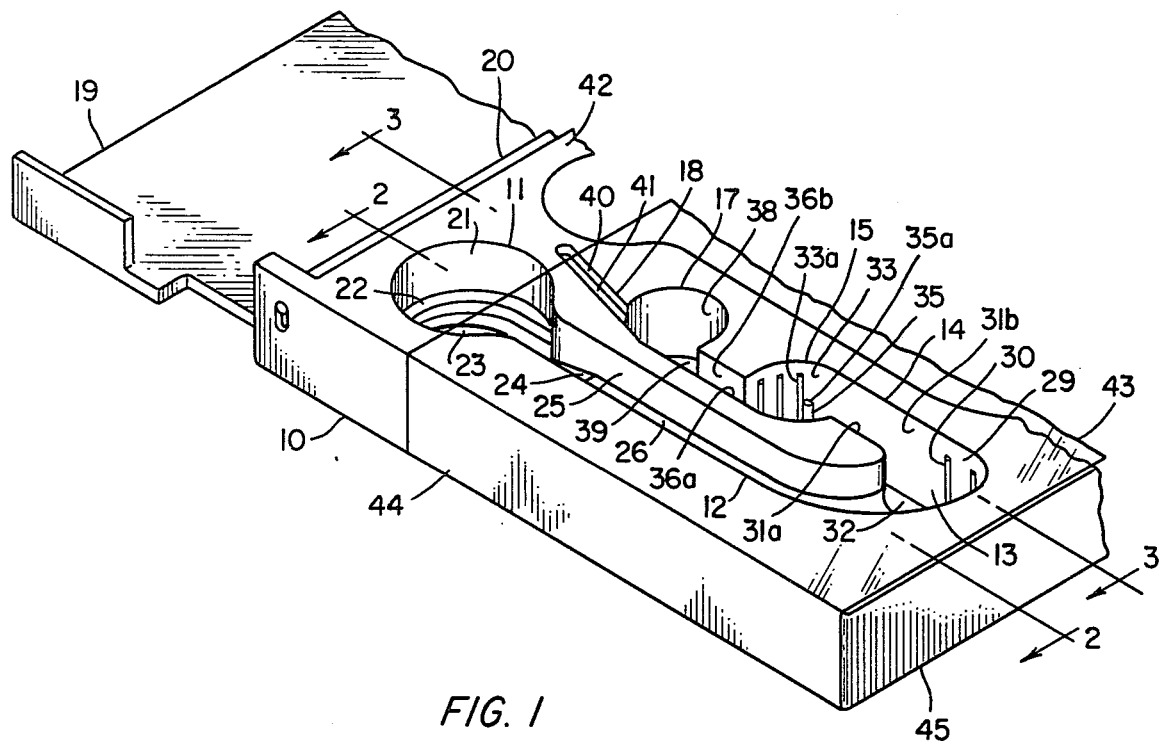
FIG. 1 is a partial perspective view of the diagnostic device of this invention.

Referring to FIG. 1, there is shown diagnostic device 10 having a plurality of transversely arrayed multiple interconnected chambers and wells for use in the identification of microorganisms. Formed in upper surface of frame or support structure 42 of device 10 is first chamber or well 11 into which a test suspension containing a bacterial culture may be pipetted. First well 11 is interconnected with second chamber or well 13 through first passage means 12. The second well is connected to third chamber or well 15 through second passage means or channel 14 and the third well is connected to fourth chamber 17 through third passage means or channel 16. A vent channel 18 connects with fourth chamber 17 to provide venting during use of the device.

Figure 2:
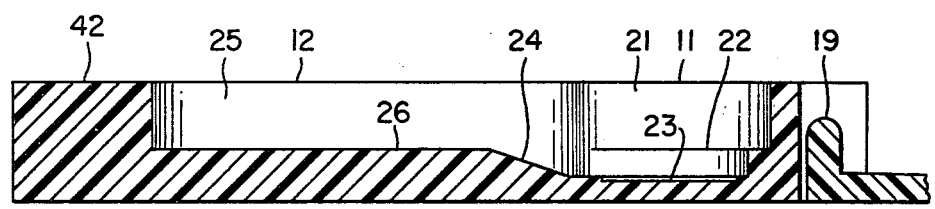
FIG. 2 is a partial cross-sectional view of a portion of the diagnostic device of FIG. 1 taken along the line 2—2.
Figure 3:
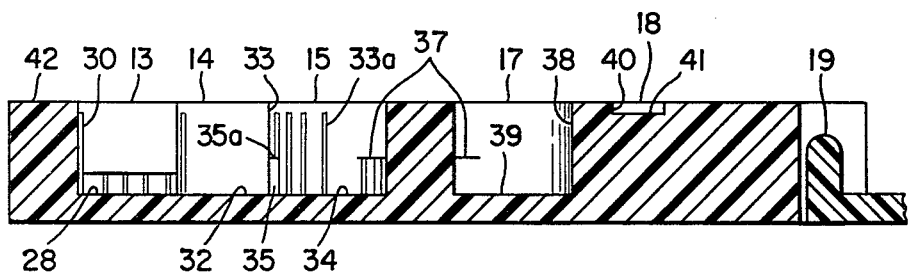
FIG. 3 is a partial cross-sectional view of the diagnostic device of FIG. 1 taken along the line 3—3.

Referring to FIGS. 2 and 3 in addition to FIG. 1, well 11 comprises an open-top chamber recessed into surface 42. Well 11 is substantially cylindrical formed by side wall 21 and terminating in base 23 which is in a plane parallel to surface 42. Shoulder 22 is an annular member formed contiguous with base 23 of well 11 resulting in a cylindrical portion of narrower diameter. A segment of wall 21 opens up into and connects with channel 12. The segment encompasses an arc of approximately 30° and walls 25 of channel 12 smoothly transition into wall 21. Base 26 of channel 12 is substantially parallel to base 23 but on a different plane, connecting with the plane of base 26 through vertically ascending ramp 24, which ramp prevents passage of the test suspension from well 11 to well 13.

Channel 12 extends radially from the axis of well 11 and parallel to margin or side 44. At its distal end, it turns transversely to join with well 13, the axis of which is transversely displaced and eccentric to the axis of well 11. Well 13 is formed by cylindrical wall 29 which is perpendicular to base 28 which is substantially parallel to base 26 and substantially co-planar with base 23. The plane of base 26 transitions to the level or plane of base 28 through a sharp cylindrical wall structure 27, forming a portion of wall 29. Axially extending ribs 30 arrayed internally of walls 29 and 27 act as interference members for the containment of a substrate disc when placed therein.

Second passage means 14 eccentrically intersects wall 29 of well 13 and extends substantially parallel with channel 12. Base 32 of passage means or channel 14 is co-planar with base 28 and intersects with vertical side walls 31a and 31b. Third chamber or well 15 is formed by cylindrical wall 33 which is vertical to base 34, which base is co-planar with base 28. The radius of wall 33 is substantially equal to that of wall 29 and contains thereon vertically extending ribs 35. Ribs 35 do not extend the entire height of wall 33 but terminate in shoulders 35a at an intermediate level. Shoulders 35a, three of which are equally spaced about wall 33, provide a seat or base upon which the detection reagent is placed, the raised position providing better visualization of a color change at completion of incubation period. Ribs 33a act to hold the substrate disc in a desired position. The axis of well 15 is in a plane containing the axis of well 13 and parallel to margin 44. Wall 31b of channel 14 is tangent with walls 29 and 33 and wall 31a intersects cylinder wall 29 and 33 in the plane containing the axes of the wells.

Third passage means 16 has perpendicularly descending walls 36a and 36b intersecting with its base 37. The plane containing base 37 is above base 34 and substantially co-planar with shoulders 35a of ribs 35. Hence the depth of the test suspension must exceed the level of base 37 and must pass over the detection reagent disc before allowing passage of liquid through channel 16. The walls 36a and 36b are substantially parallel to walls 25 of channel 12, and wall 36b is in the same plane as wall 31a. Wall 36a intersects cylindrical wall 33 at a radius extending perpendicular thereto and hence is tangent to the radius of wall 33 at that point.

Channel 16 interconnects with chamber 17, which chamber comprises cylindrical wall 38 vertically intersecting with base 39, which is co-planar with base 34. Vent means 18 comprises a channel having vertically extending walls 40 intersecting with base 41. Base 41 is parallel to the plane of surface 42 and intersects with wall 38 of chamber 17. Channel 18 permits the escape of any volatiles produced by the reagents and any trapped air resulting from introduction of the test suspension.

All wells and channels of the device are open with respect to surface 42. Channels 12, 14 and 16 and wells 13, 15 and 17 are covered by a transparent adhesive film 43, which film is impervious to air and moisture but allows clear visual inspection of the interior. Transparent member 43 covers only a portion of vent means 18 thereby allowing for the escape of volatiles through the unsealed portion thereof. Chamber 11 remains unsealed and open to the environment in order to permit inoculation of the chamber with the test culture or suspension. In the preferred embodiment of this invention, a plurality of test chambers and channels are arrayed in parallel so that a plurality of different tests may be performed at the same time while utilizing a single diagnostic device. The support structure and test chambers may be integrally molded of high impact polystyrene as well as other suitable plastics. A hinged over plate 19 is provided along a rear margin of the test structure and is hinged on axis 20 for closure of wells 11 when cover 19 is rotated into mating condition with surface 42. The inside surface of cover 19 may be covered with a bibulous or other absorbent material to take up excess test suspension when in a closed position, which absorbent material may contain a germicidal agent; also the inside cover may contain suitable indicia to identify the tests to be performed in each successive chamber.

The unit 10 is generally designed to have rounded corners and an absence of sharp edges. This feature permits storage of the device in airtight sealed pouches without danger of puncture which would result in degradation of performance due to the presence of air and moisture. The device may also be packaged with desiccants to avoid moisture damage.

Figure 4:
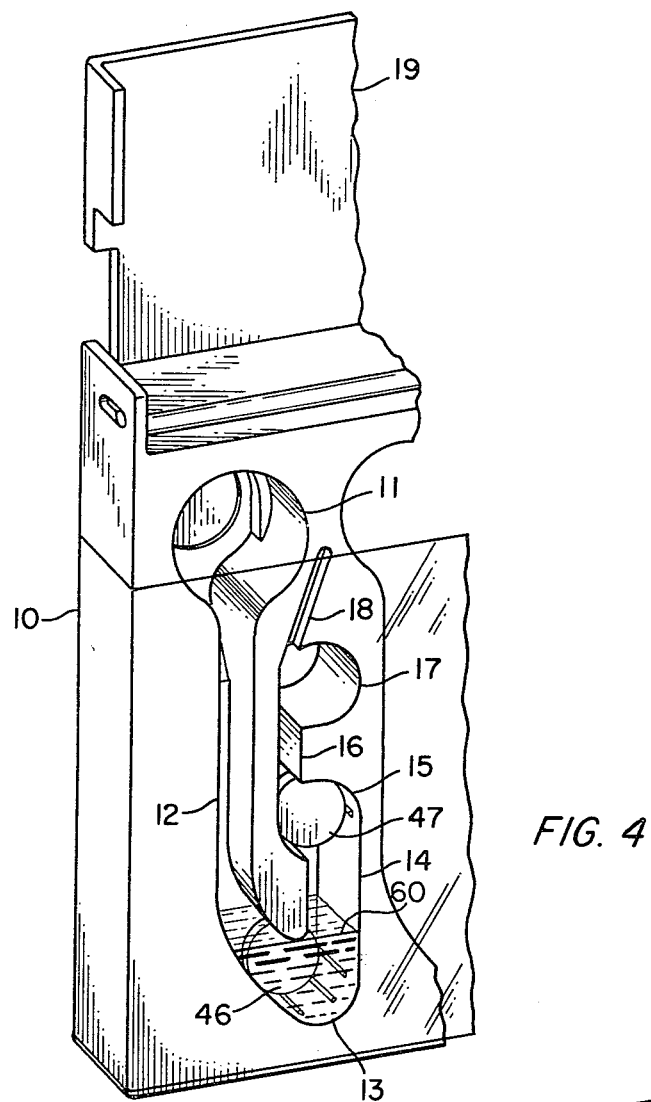
FIG. 4 is a partial perspective schematic view of the diagnostic device of FIG. 1 shown in a specific orientation.
Figure 5:
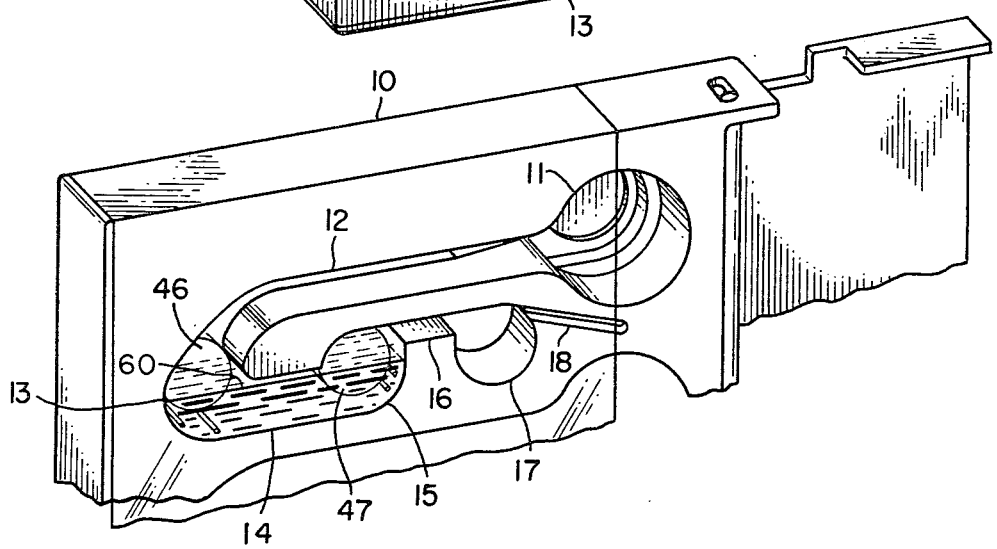
FIG. 5 is a partial perspective schematic view of the diagnostic device of FIG. 1 shown in another spatial orientation.

Referring now to FIGS. 4 and 5, a typical use of the diagnostic device may be reviewed. With device 10 in a substantially horizontal plane as depicted in FIG. 1, well 11 may be inoculated with a test suspension of the culture formed from the suspected specimen. After inoculation, device 10 is rotated about an axis parallel to margin 45 so as to assume a substantially 90° vertical position. In this position inoculant 60 is caused to proceed over ramp 24 and through channel 12 into well 13. In well 13 a disc 46 formed from bibulous paper containing a substrate reagent is located and held in position by ribs 30. For example, as set out in U.S. Pat. No. 3,645,853, an impregnated paper strip may be prepared in accordance therewith and a disc made therefrom may be used to perform a nitrate reduction test. With the disc substrate in contact with liquid inoculant 60, device 10 in the indicated spatial orientation is incubated for a period of approximately four hours at a temperature of 35°-37° C. In a positive test, the enzyme, nitrate reductase, produced in almost 100% of cultures belonging to the family Enterobacteriaceae and by certain other bacteria, acts to reduce the nitrate contained in the substrate zone disc. Subsequent to the incubation period, device 10 is rotated about an axis perpendicular to the plane of surface 42 approximately 90° as indicated in FIG. 5. Device 10 is manipulated about this position to cause the reacted test suspension to come into contact with the indicator disc 47 located in third chamber 15. If nitrate has been reduced to nitrite the nitrite is detected by a reaction with sulfanilic acid and an alpha naphthylamine derivative on the detection disc, a red color end product is produced and a positive indication derived. Excess test suspension may escape into chamber 17 and volatiles may escape through vent channel 18.

In one proposed use of device 10, a number of different tests are performed, namely: Voges-Proskauer, nitrate reductase, phenylalanine deaminase, hydrogen sulfide, indole, ornithine decarboxylase, lysine decarboxylase, malonate utilization, urease, esculin hydrolysis, ONPG, and arabinose, adonitol, inositol, and sorbitol fermentations. Using these tests, a substantial number of different Enterobacteriaceae identifications may be made with a high degree of accuracy, e.g., species differentiation within the genera Escherichia, Shigella, Edwardsiella, Salmonella, Arizona, Citrobacter, Klebsiella, Enterobacter, Serratia, Proteus, Providencia and Yersinia. Of course, this device may be used with other combinations of biochemical tests to identify the same as well as other organisms.

The following tables set forth the identity of known cultures and the percent accuracy of their identification using the novel device of applicants' invention:

TABLE I

Identity of 440 cultures used in this study

| Organism | Number | Organism | Number |
|---|---|---|---|
| Escherichia | 115 | Serratia marcescens | 11 |
|  |  | S. liquefaciens | 6 |
| Shigella spp. | 5 | S. rubicaea | 4 |
| S. sonnei | 3 |  |  |
|  |  | Proteus vulgaris | 12 |
| Edwardsiella tarda | 1 | P. mirabilis | 51 |
|  |  | P. morganii | 14 |
| Salmonella typhi | 1 | P. rettgeri | 8 |
| S. enteritidis | 12 |  |  |
| S. cholerae-suis | 0 | Providencia alcalifaciens | 5 |
|  |  | P. stuartii | 7 |
| Arizona hinshawii | 3 |  |  |
|  |  | Yersinia enterocolitica | 4 |
| Citrobacter freundii | 10 | Y. pseudotuberculosis | 0 |
| C. diversus | 5 | Y. pestis | 0 |
| Klebsiella pneumoniae | 77 |  |  |
| K. rhinoscleromatis | 3 |  |  |
| K. ozaenae | 10 |  |  |
| Enterobacter cloacae | 30 |  |  |
| E. aerogenes | 29 |  |  |
| E. hafniae | 7 |  |  |
| E. agglomerans | 7 |  |  |

TABLE II

Accuracy of Individual Micro-ID Biochemical Tests Compared to Conventional Tests Using Fresh Clinical Isolates

| Biochemical Test | No. Correct/No. Tested | Percent Accuracy |
|---|---|---|
| Voges-Proskauer | 427/440 | 97.0% |
| Nitrate Reductase | 434/440 | 98.6% |
| Phenylalanine Deaminase | 436/440 | 99.1% |
| $H_2S$ | 427/440 | 97.1% |
| Indole | 434/440 | 98.6% |
| Ornithine Decarboxylase | 431/440 | 98.0% |
| Lysine Decarboxylase | 425/440 | 96.6% |
| Malonate | 434/440 | 98.6% |
| Urease | 421/440 | 95.7% |
| Esculine | 438/440 | 99.6% |
| ONPG | 433/440 | 98.4% |
| Arabinose | 435/440 | 98.9% |
| Adonitol | 433/440 | 98.4% |
| Inositol | 430/440 | 97.7% |
| Sorbitol | 432/440 | 98.2% |

In view of the foregoing, it is apparent that the applicants have invented a diagnostic device permitting the rapid and accurate identification of large numbers of microorganisms. The device is a highly efficient disposable unit which expedites the test procedure and reduces the probability of error. It overcomes the disadvantages of the prior art and improves on existing methods and apparatus. In sum, applicants have produced a unitary disposable device in which a first chamber may be inoculated with an unknown test suspension. The test suspension is conducted through a channel to a second chamber containing an identifying reagent by orienting the device to a particular spatial position. After incubation for a predetermined period and temperature, the reacted fluid is then passed through another channel by orienting the device to yet another position. The action of the reagent and the indicator with the test suspension permits the rapid garnering of accurate identification data.

The foregoing description and drawings are intended to be illustrative of applicants' invention and all modifications apparent to one of ordinary skill in the art are considered to be within its ambit.

What is claimed is:

1. An improved diagnostic device comprising, a frame of substantially planar form having a transversely extending margin, which has a top surface into which are recessed a first well for containing a liquid test suspension, a second well for contacting the test specimen with a reagent and a third well for contacting the reacted test suspension with an indicator; wherein through the arrangement of the frame to a predetermined first spatial orientation a liquid communication between the first and second wells can be provided when the frame is rotated from its normal horizontal position about a first axis running parallel to a margin of the frame; and wherein further through the arrangement of the frame to a predetermined second spatial orientation a liquid communication between the second and third wells can be provided, said improvement comprising a first channel extending from the first well toward the transversely running margin of the frame providing for liquid communication between the first and second wells, said channel turning substantially parallel to the margin at its distal end to intersect the second well, the second well being transversely displaced from the first well; a second channel extending away from the margin substantially parallel to the first channel providing for liquid communication between the second and third wells, the second channel intersecting the third well, and the third well being substantially aligned with the second well; said wells and said channels between said wells being open to said top surface and a clear transparent film is provided in adhesive sealing contact with the top surface of the frame covering the wells, except the first well, whereby the first axis, about which the frame is rotated from its normal horizontal position in order to provide for liquid communication between the first and second wells, runs parallel to the transversely extending margin; and further providing for liquid communication between the second and third wells when the frame is rotated about a second axis, which is perpendicular to the top surface of the frame.

2. The device of claim 1 wherein a fourth well is provided for containing the overflow of the test suspension from the third well and the fourth well is connected with the third well through a third channel.

3. The device of claim 2 wherein the third channel has walls which are substantially parallel to the first channel and a base which is substantially parallel to and located intermediate of the planar surface and the base of the third well.

4. The device of claim 2 wherein the wells are of substantially cylindrical shape extending vertically from the planar surface of the frame.

5. The device of claim 4 wherein the third channel has a first wall which is tangent to the third and fourth wells and a second wall in a plane containing the axes of the second and third wells.

6. The device of claim 5 wherein the fourth well has an axis contained in the plane of the axes of the second and third wells, and the second, third and fourth wells have substantially the same diameter.

7. The device of claim 2 wherein a vent channel is provided, the vent channel extending vertically from the planar surface at a level intermediate the planar surface and the base of the fourth well, the vent channel interconnecting with the fourth well.

8. The device of claim 7 wherein the third channel and the vent channel are substantially rectangular in cross-section.

9. The device of claim 7 wherein the transparent film covers a portion of the vent channel in a sealing manner.

10. The device of claim 9 wherein the frame contains a cover hingedly mounted thereto for covering the first well and the vent channel when placed in a complementary mating position with the planar surface of the frame.

11. The device of claim 10 wherein the inner surface of the cover contains an absorbent means for containing liquid suspension and the absorbent means contains a germicidal agent.

12. The device of claim 1 wherein the liquid communication between the first and second wells is provided when the frame is rotated about the first axis by approximately 90° from the normal horizontal position.

13. The device of claim 12 wherein the liquid communication between the second and third wells is provided when the frame is rotated about the second axis by approximately 90°.

14. The device of claim 1 wherein the second channel is substantially perpendicular to the transversely extending margin.

15. The device of claim 1 wherein the first channel contains a vertically ascending ramp member in its base to prevent liquid communication between the first and second wells and to allow liquid communication therebetween when the frame is moved to the predetermined first spatial orientation.

16. The device of claim 1 wherein the reagent is in the form of a substrate disc located in the second well.

17. The device of claim 16 wherein a reagent in the form of a detection disc is located in the third well.

18. The device of claim 17 wherein the walls of the second and third wells contain vertically arrayed ribs for holding the discs in a desired orientation.

19. The device of claim 11 wherein the first channel extends radially from the first well in a direction substantially perpendicular to the transversely extending margin, the first channel having an arcuate transverse displacement at its distal end connecting with the second well, the second well having an axis transversely displaced of the axis of the first well and in a plane perpendicular to the transversely extending margin and containing the axis of the third well, the second and third wells having bases substantially coplanar with the base of the first well, the third well being interposed between the second well and the transversely extending margin, and the second channel having a first wall lying in the plane containing the axes of the second and third wells and a second wall transversely displaced from the first wall in a plane tangent to the second and third wells.

20. The device of claim 11 wherein the frame is transversely extended and contains a plurality of individual diagnostic devices in serial parallel array.

21. The device of claim 20 comprising an integral molded plastic unit.

22. An improved diagnostic device comprising, a frame of substantially planar form having a transversely extending margin, which has a top surface into which are recessed a first well for containing a liquid test suspension, a second well for contacting the test specimen with a reagent and a third well for contacting the reacted test suspension with an indicator; wherein through the arrangement of the frame to a predetermined first spatial orientation a liquid communication between the first and second wells can be provided when the frame is rotated from its normal horizontal position about a first axis running parallel to a margin of the frame; and wherein further through the arrangement of the frame to a predetermined second spatial orientation a liquid communication between the second and third wells can be provided, said improvement comprising a first channel extending from the first well toward the transversely running margin of the frame providing for liquid communication between the first and second wells, said channel turning substantially parallel to the margin at its distal end to intersect the second well, the second well being transversely displaced from the first well; a second channel extending away from the margin substantially parallel to the first channel providing for liquid communication between the second and third wells, the second channel intersecting the third well, and the third well being substantially aligned with the second well; a fourth well is provided for containing the overflow of the test suspension from the third well and the fourth well is connected with the third well through a third channel; and a vent channel is provided, the vent channel extending vertically from the planar surface at a level intermediate the planar surface and the base of the fourth well, the vent channel interconnecting with the fourth well, whereby the first axis, about which the frame is rotated from its normal horizontal position in order to provide for liquid communication between the first and second wells, runs parallel to the transversely extending margin; and further providing for liquid communication between the second and third wells when the frame is rotated about a second axis, which is perpendicular to the top surface of the frame.

23. An improved diagnostic device comprising, a frame of substantially planar form having a transversely extending margin, which has a top surface into which are recessed a first well for containing a liquid test suspension, a second well for contacting the test specimen with a reagent and a third well for contacting the reacted test suspension with an indicator; wherein through the arrangement of the frame to a predetermined first spatial orientation a liquid communication between the first and second wells can be provided when the frame is rotated from its normal horizontal position about a first axis running parallel to a margin of the frame; and wherein further through the arrangement of the frame to a predetermined second spatial orientation a liquid communication between the second and third wells can be provided, said improvement comprising a first channel extending from the first well toward the transversely running margin of the frame providing for liquid communication between the first and second wells, said channel turning substantially parallel to the margin at its distal end to intersect the second well, the second well being transversely displaced from the first well; a second channel extending away from the margin substantially parallel to the first channel providing for liquid communication between the second and third wells, the second channel intersecting the third well, and the third well being substantially aligned with the second well; a vent channel communicatingly connected with the third well; and wherein the frame contains a cover hingedly mounted thereto for covering the first well and the vent channel when placed in a complementary mating position with the planar surface of the frame, the inner surface of the cover containing an absorbent means for containing liquid suspension and the absorbent means contains a germicidal agent, whereby the first axis, about which the frame is rotated from its normal horizontal position in order to provide for liquid communication between the first and second wells, runs parallel to the transversely extending margin; and further providing for liquid communication between the second and third wells when the frame is rotated about a second axis, which is perpendicular to the top surface of the frame.

* * * * *